United States Patent [19]

Kubo et al.

[11] 4,287,760

[45] Sep. 8, 1981

[54] METHOD AND EQUIPMENT TO MEASURE FAT CONTENT OF MEAT

[75] Inventors: Shinji Kubo, Chiba; Norio Yamada, Ichikawa, both of Japan

[73] Assignee: Chibayaku Groceries, Incorporated, Chiba, Japan

[21] Appl. No.: 76,309

[22] Filed: Sep. 17, 1979

[30] Foreign Application Priority Data

Dec. 4, 1978 [JP] Japan .............................. 53-149089

[51] Int. Cl.³ ..................... G01F 17/00; G01N 9/10
[52] U.S. Cl. .................................. 73/149; 73/32 R; 73/450
[58] Field of Search .............. 73/450, 444, 1 H, 32 R, 73/149

[56] References Cited

U.S. PATENT DOCUMENTS

| | | | |
|---|---|---|---|
| 1,075,477 | 10/1913 | Hutchinson | 73/450 |
| 2,889,703 | 6/1959 | Lipson et al. | 73/32 R |
| 3,557,625 | 1/1971 | Leger, Jr. et al. | 73/432 R |
| 4,010,934 | 3/1977 | McCord et al. | 366/142 |
| 4,027,860 | 6/1977 | Mamvriisky | 366/142 X |
| 4,144,749 | 3/1979 | Whitmore | 73/149 |

FOREIGN PATENT DOCUMENTS

| | | | |
|---|---|---|---|
| 49676 | 3/1889 | Fed. Rep. of Germany | 73/32 R |
| 510374 | 8/1926 | Fed. Rep. of Germany | 73/32 R |
| 629447 | 4/1936 | Fed. Rep. of Germany | 73/32R |
| 987206 | 8/1951 | France | 73/450 |

OTHER PUBLICATIONS

Publ., "Precision Measurement of Density", Nat'l. Bureau Standards Technical News Bulletin, vol. 56, No. 2, Feb. 1972.

*Primary Examiner*—Daniel M. Yasich
*Attorney, Agent, or Firm*—William W. Haefliger

[57] ABSTRACT

A method of measuring fat content of meat includes the steps of immersing a meat sample in a liquid, and detecting the amount of displacement of the liquid by the meat sample, the variance of such displacement as a function of fat content being predetermined, whereby the fat content is determinable from the detected displacement.

3 Claims, 5 Drawing Figures

4,287,760

METHOD AND EQUIPMENT TO MEASURE FAT CONTENT OF MEAT

BACKGROUND OF THE INVENTION

This invention concerns a unique method by which the fat content degree of meat can be measured by putting a fixed amount of meat into liquid which will not dissolve fat, and by measuring the specific gravity or the specific volume of the meat. It also includes the measuring equipment to determine fat content composed of an apparatus using a measuring point that is fixed by known sample in advance, and ways with which the specific gravity or the specific volume of the meat can be measured.

The ratio of flesh and fat in meat can be relative to its price at any butcher shop or supermarket. The flesh part of meat is mostly protein and the white part is almost all fat. The optimum proportions can be varied depending on the use or consumer desire. In sliced or ground meat, most consumers are dissatisfied with more fatty meat than that with more flesh part in store displays. Therefore, they value the meat with a smaller fat content as having high quality, and that with high fat content as associated with lower quality.

Presently, the fat content degree is measured by using the method of heating ground meat and weighing the volume of fat content after separating fat from flesh, the melting point of beef fat being lower than the melting point of the flesh part. (Fat Percentage Indicator—Hobart Corporation, U.S.A.) In this method, fat content is measured by heating 50 grams of ground meat for 20 minutes. Over 25 minutes, at least, is required for measuring. In addition, the volume of melted fat separated from the meat will vary depending on the temperature of the test room. It is useless to measure, by use of the fat percentage indicator, (hereafter called the indicator) in a room where the temperature is below 18 degree C. In order to maintain the freshness of meat, two degrees below zero is required. In the meat processing room, room temperature will commonly be kept below 15 degrees C. Therefore, the indicator has little value, under these circumstances.

The melting point of beef fat is 40° C.–50° C. and that of pork is 33° C.–40° C. The aforementioned indicator is devised for measuring fat content degree of beef only. If we were to measure fat content of pork, it would be necessary to change the temperature used in heating it and the time of heating.

Because of the above mentioned reasons, the present invention is aimed to provide method and equipment for measuring fat content degree which can be operated with ease in the process room in order to give consumers the proper information about fat content ratio. The information presents correct measurement of fat content to consumers and offers the opportunity for better sales to retailers.

SUMMARY OF THE INVENTION

An important characteristic of this invention is that fat content ratio can be measured by using the specific gravity or the specific volume of meat because there is a difference of specific gravity between the flesh and fat part of meat.

Basically, the method of the invention involves the following steps:
(a) immersing a meat sample in a liquid, and
(b) detecting the amount of displacement of the liquid by the meat sample, the variance of such displacement as a function of fat content being predetermined, whereby the fat content is determinable from the detected displacement.

As will be seen, the meat is immersed in the liquid (as for example water) in either ground state, sliced state or block state.

More specifically, one of the methods contemplated includes the use of a container for said liquid and a floating liquid height gage associated with the container and communicating with the container interior, and wherein said immersion step includes placing the meat into the container, and said detection step includes observing the height of the gage as a consequence of the immersion of the meat in the container. Further, the gage typically has an associated calibration indicia to show different height levels corresponding to different meat fat contents, and said detection step includes observing the height of the calibration of indicia.

Another method contemplates use of a container for said liquid and a hydrostatic balance to float in said liquid, and wherein said immersion step includes attaching the meat in load transfer relation with the balance to be immersed in the liquid with the balance then floating in the liquid, and said detection step includes observing the vertical positioning of the balance relative to the liquid surface level. As before, the gage has associated calibration indicia used as described above.

An alternative method involves the use of a lower container, an upper container, and a liquid height gage between the containers, and wherein said immersion step includes filling a predetermined quantity of said liquid into the upper container, placing the meat into the lower container, and flowing liquid from the upper container into the lower container, and said detection step includes observing the height of liquid standing in the gage as a consequence of said immersion of the meat in the lower container. Finally, another method involves use of first and second containers and a tubular liquid height gage interconnecting said containers, and wherein said immersion step includes filling liquid into the first container in a lower position and placing the meat sample into the second container in an upper position, closing the second container, moving the first container into an upper position, and the second container into a lower position and also flowing liquid from the first container into the second container via said gage, and said detection step includes observing the height of the liquid standing in the gage as a consequence of said immersion of the meat in the second container. In each of these methods, liquid level height gages are usable, as described above.

These and other objects and advantages of the invention, as well as the details of an illustrative embodiment, will become more fully understood from the following specification and drawings, in which:

DRAWING DESCRIPTION

GENERAL DESCRIPTION

Initially, the following mathematical considerations are of importance.

Let the fat content ratio of meat be designated as X wt.%.

Let the weight of sliced, block or ground meat (containing X wt.% fat) be designated as Wx.

Let the volume of the meat be designated as Vx.

Then, the following relationships are established:

$$Wr = Wx\left(1 - \frac{X}{100}\right)$$

$$Wf = Wx \cdot \frac{X}{100}$$

$$Vx = \frac{Wr}{pr} + \frac{Wf}{pf} = \frac{Wx \cdot X}{100}\left(\frac{1}{pf} - \frac{1}{pr}\right) + \frac{Wx}{pr}$$

or, $$\frac{Vx}{Wx} = \frac{1}{px} = vx = \frac{X}{100}\left(\frac{1}{pf} - \frac{1}{pr}\right) + \frac{1}{pr}$$

where,
- Wr = fresh part weight (gr) of Wxgr weight of meat which contains Xwt% fat.
- Wf = fat part weight (gr) of Wxgr weight meat which contains Xwt% fat.
- pf = specific gravity of fat part; gr/ml
- pr = specific gravity of fresh part; gr/ml
- px = specific gravity of meat with Xwt% fat; gr/ml
- vx = specific volume of meat with Xwt% fat; ml/gr Therefore, correct figures about fat content ratio (degree of fat part) can be easily achieved if px or vx is measured by preparing a measuring mark after counting specific gravity or specific volume of a model sample which has an appointed i.e. known mixture ratio of flesh and fat.

The degree of fat content is varied depending on each classification of meat, i.e., beef, pork, chicken, etc. In addition, they are classified not only to kind of items as block meat, sliced meat, ground meat, but also to several grades. The equipment described herein operates very easily and figures can be obtained without delay and scores of meat samples can be tested within a day.

Figure 1:
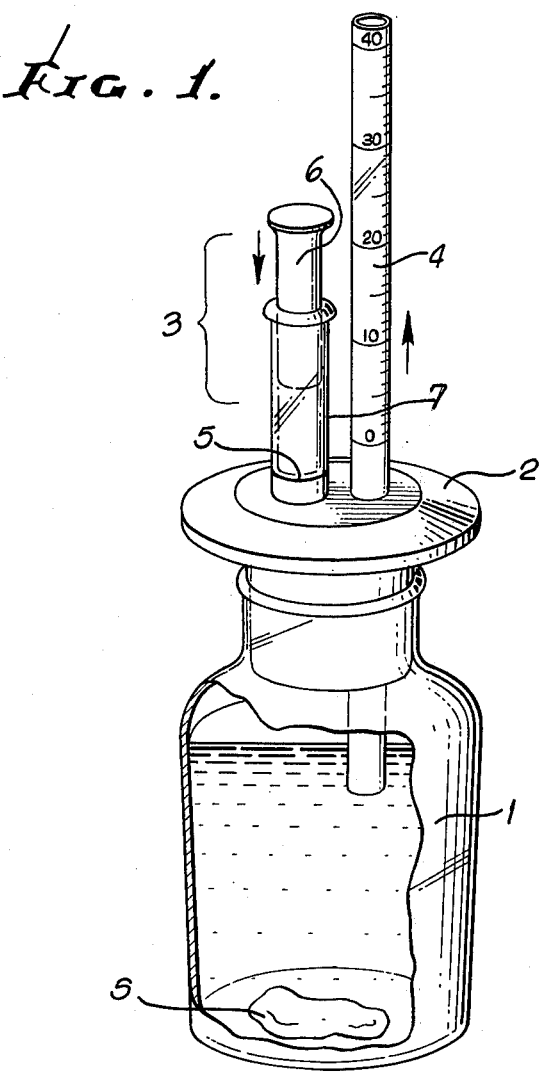
FIG. 1 is an elevation showing one form of apparatus for carrying at the invention.

FIG. 1 shows that a piston pump 3 with a floating plunger and bullet 4 (i.e. liquid level height gage) set passing through the lid 2 vertically covering the flask 1. The liquid put or accessed into flask 1 should be one which will not dissolve fat. Here we use usual drinking water from the city water-supply system. First mark a measuring point on the bullet 4 as follows: separate flesh part and fat part from pork as model sample, and prepare one sample with flesh part only and others mixed with 10, 20, 30% fat content . . . (weight %). Then adjust this sample to ground meat containing each weight % of fat. Weigh each sample of ground meat at 50 grams beforehand. Use 500 ml capacity of flask 1 in this experiment. Prepare 505 ml water to a temperature of 18 degrees C.

Open the lid 2.
Pour 400 ml water into flask.
Put ground meat, (flesh part only i.e. fat content zero) with slight shake, into flask.
Close the lid.
Pull out the plunger 6 from the pump 3.
Put 105 ml of remaining water via pump 3 into flask. The level of water in the pump should be higher than mark 5.
Use the cylinder 7 of piston pump 3 with 1.5 cm diameter inside and 10 cm long for this test.
The inside diameter of the bullet should be 0.7 cm and 6 cm long.
Insert the plunger in the piston pump and push down slowly, then the water in the piston pump is pushed down into the flask and the level of water in the bullet is pushed up. When the lower edge of the plunger is set on the mark 5 at the bottom of cylinder of the piston pump, enter the figures of water level in bullet 4 on the bullet 4 as measuring point of 0 mark. Similarly when one puts test ground meat containing 10%, 20%, 30% fat . . . (weight %) into each flask 1, the water level of bullet 4 comes up according to the specific volume of ground meat in proportion to the fat content degree. Then enter the figures marked with degree of water level . . . 10, 20, 30, etc.

Now one can examine the degree of fat content without difficulty, by measuring the water level indicated by the floating bullet 4, putting 50 gram weight of meat for experiment S into flask 1.

The following table is a result of accuracy comparison of each, measured by the present method, as compared with the known indicator and "Ether extraction" method

|  | Figures of fat content degree | Measuring time |
| --- | --- | --- |
| Present test #1 | 25, 23, 28 | 4 minutes |
| Indicator | 23, 25, 23 | 30 minutes |
| "Etherextraction" method | 21, 23 | 16 hours |

The result of test #1 shows that accuracy is almost the same as tests of "Ether extraction" method.

Figure 2:
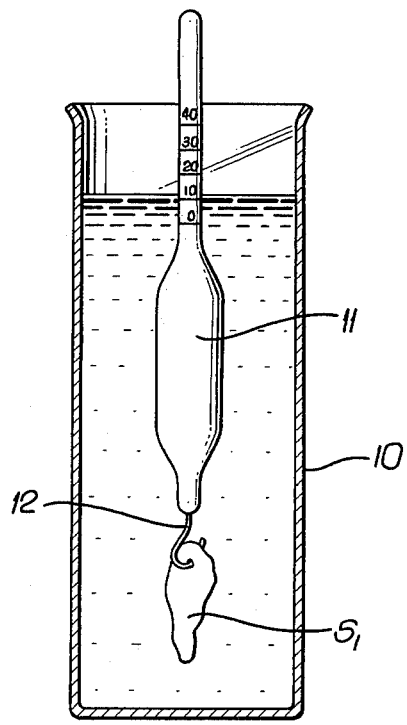
FIG. 2 is an elevation showing another form of apparatus to carry out the invention.

The equipment shown in FIG. 2 includes a glass cylinder 10 and a hydrostatic balance 11. At the bottom of the hydrostatic balance, hook 12 is set and a piece of meat $S_1$ can be hung from it. It is almost the same as test #1 regarding how to set measuring point with this equipment.

First the flesh and fat parts of pork are separated. Prepare the flesh part only, with one containing 10% fat, one 20%, and one 30% . . . (weight %), and scale each piece of meat just at 20 grams. Pour water into glass pipe 10, hang a piece of meat with flesh part only from hook 12 at the hydrostatic balance, then put it in the water. The place where the hydrostatic balance 11 and water level will meet is marked "0" as the measurement point. If we hang a piece of meat containing 10% weight fat from hook 12, hydrostatic balance will rise up higher than in the case of putting flesh part only, because the gravity of meat containing fat part becomes light in proportion to the volume of fat. So set the place where the hydrostatic balance and water level will meet as "10" measuring point.

Similarly, hang a piece of meat containing 20%, 30% fat . . . (weight %) from the hydrostatic balance 11 and set each measuring point at the flask. When 20 grams of meat for test $S_1$ is hung from hook 12 and placed into the water of glass cylinder 10, the figures of the place where water level and the hydrostatic balance will meet show the degree of fat content of meat for that test. If one wants to measure ground meat by this equipment, one can use a wire net to hold the meat.

The following table shows results obtained when 20 grams of pork were measured using the equipment of this test #2:

|  | Figures of fat content degree | Measuring time |
|---|---|---|
| Present test #2 | 24, 24, 25 | 5 minutes |
| Indicator | 18, 20, 15 | 25 minutes |
| Ether extraction method | 22 | 18 hours |

Test #2 is more accurate than the indicator, and the results show nearly the same figures as the ether extraction method. Also, measuring time was very short.

Figure 3:
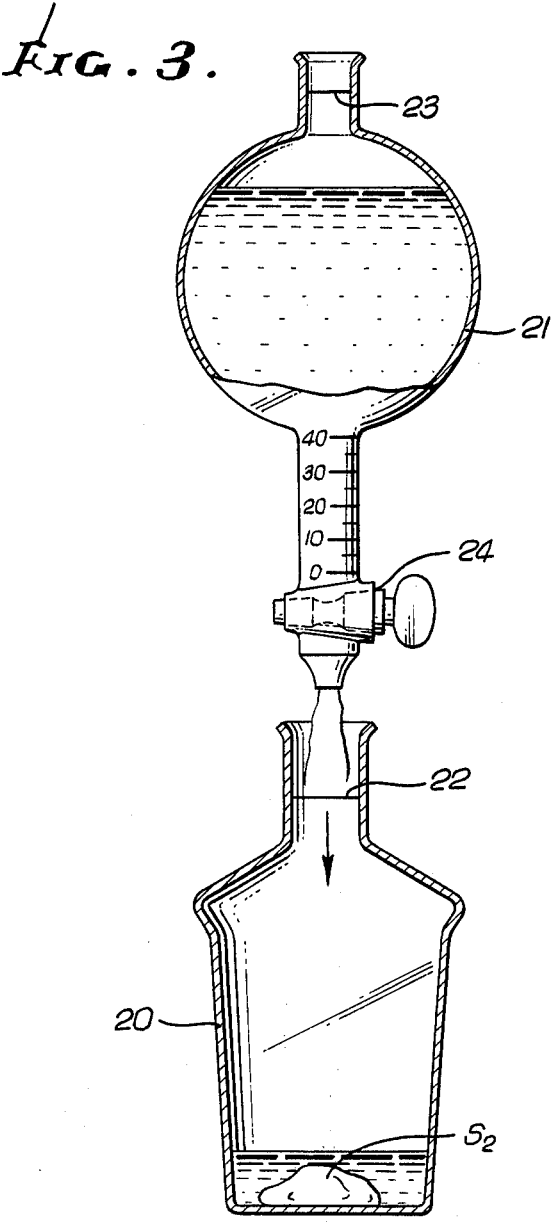
FIG. 3 is an elevation showing a further form of apparatus to carry out the invention.

The FIG. 3 equipment includes flask 20 and bullet 21 and we mark point 22, 23 at the top of flask 20 and bullet 21 beforehand.

Prepare 50 grams of meat with flesh part only and one containing 10%, 20%, 30% fat ... (weight %).

Put water into bullet 21 up to the point 23.

Put 50 grams of flesh meat into flask 20, open the stopper 24 of bullet 21 and pour water up to the point 22 of flask. While doing this, shake flask 20 occasionally, to release bubbles in meat.

Close the stopper 24 when water reaches the point 22 of flask 20.

Water level remaining in bullet 21 is marked "0".

Then put ground meat containing 10%, 20% or 30% fat ... (weight %) into the flask, and release the water of bullet 21 into flask 20.

The remaining water in the bullet will be increased accordingly as the volume of ground meat will be increased in proportion to the fat content degree. So mark each figure 10, 20, 30 ... as measuring point on the bullet 21. The measuring method of this equipment:
1. Put 50 grams of meat sample $S_2$ of unknown fat content into flask 20.
2. Pour water of bullet 21 into flask.
3. Some water will remain in the bullet.
4. A figure of fat content degree can be obtained by the level of the remaining water in the bullet.

Following are figures obtained using the fat content degree of 50 grams of sliced loin pork.

|  | Figures of fat content degree | Measuring time |
|---|---|---|
| Present test #3 | 25, 28, 29 | 1 minute |
| Indicator | 24, 24, 27 | 26 minutes |

Measuring time is one-twenty sixth shorter than the indicator, using above described #3 equipment.

Figure 4:
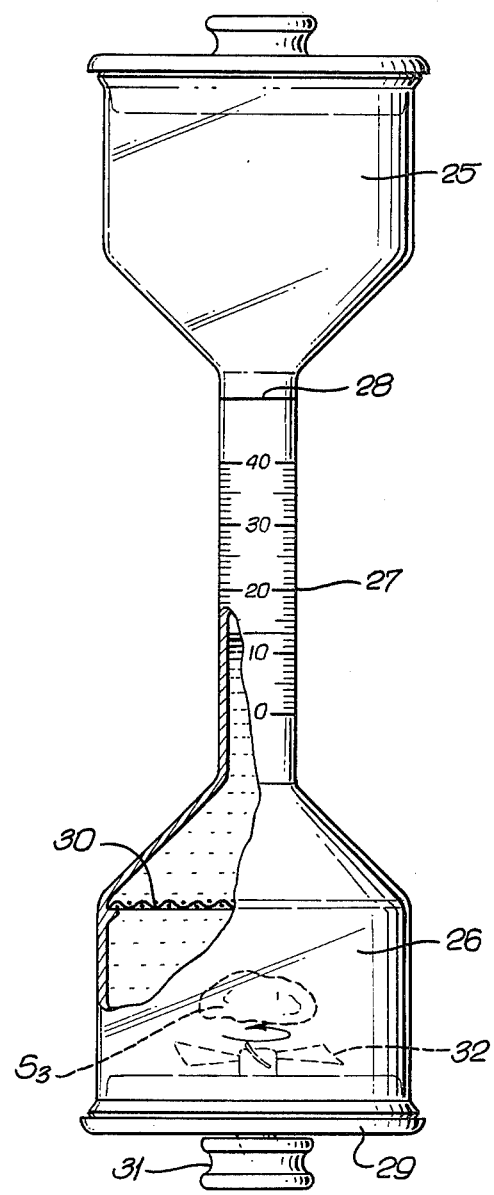
FIGS. 4 and 4a are elevations showing yet another form of apparatus to carry out the invention.
Figure 4A:
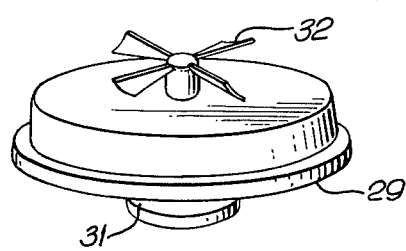

The FIGS. 4 and 4a equipment includes two flasks 25 and 26 and one bullet 27 or liquid height gage connected to the two flasks. The gage or bullet is tubular and connects the two flasks.

Mark point 28 on the top of bullet.

Prepare each 50 grams of ground meat with flesh part only and one containing 10%, 20%, 30% fat ... (weight %).

Set up flask 25 on desk, open the stopper 29, pour water up to the point 28. Then put 50 grams flesh part only into the flask 26 with wire net 30 and join the stopper 29 to the flask 26.

Invert the equipment flask 26 downwards and set it up on the desk.

Water in the flask 25 comes down into the flask 26. Then turn the screw 31 to revolve the propeller 32 and thereby disperse the ground meat in the flask 26.

When the propeller stops revolving, mark the water level of bullet 27 as 0 point.

As the volume of displaced water in the bullet 27 will be increased in proportion of the fat content degree when one puts ground meat containing fat 10%, 20%, 30% ... (weight %) into the flask, the remaining water in the bullet will increase accordingly. Then mark 10, 20, 30 ... as the measuring points on the bullet 27.

Method for using this FIG. 4 equipment:

Set flask 25 downwards, pour water up to point 28, put 50 grams of meat for test $S_3$ into the flask 26 with wire net, secure the lid 29, join it to the flask 26 and then elevate the flask 25 by inverting the equipment turning the flask 26 downwards.

In order to let ground meat spread well, revolve the propeller 32.

One can read each figure of graduation on which the water level is marked in proportion to the degree of fat content, after the propeller stops rotating.

Following are figures that were obtained when measuring the fat content degree of 50 grams of pork meat:

|  | Figures of fat content degree | Measuring time |
|---|---|---|
| Present test #4 | 23, 27, 25 | 2 minutes |
| Indicator | 24, 25, 25 | 26 minutes |

Measuring time is one-thirteen shorter than the indicator.

Advantages of this invention include the following:
1. Not necessary to heat meat
2. Time saved in measuring
3. Various kinds of meat can be tested
4. High average of accuracy
5. Simple operation.

We claim:

1. In apparatus for measuring fat content of meat, the combination comprising
   (a) a first container to receive liquid into which a meat sample is immersed when the meat sample is placed in the container, and
   (b) means associated with the container for indicating the amount of displacement of the liquid by the meat sample, the variance of such displacement being a function of fat content to be determined, whereby the fat content can be determined from the detected displacement,
   (c) said means including a liquid height gage communicating with the container interior, there being meat fat content calibration indicia vertically spaced on the gage to indicate fat content percentages, and there also being a piston pump on a lid for the container, said lid providing means via which liquid is accessed into the container, said height gage projecting upwardly through the lid to receive liquid displaced by the pump.

2. In apparatus for measuring fat content of meat, the combination comprising
   (a) a first container to receive liquid into which a meat sample is immersed when the meat sample is placed in the container, and
   (b) means associated with the container for indicating the amount of displacement of the liquid by the meat sample, the variance of such displacement being a function of fat content to be determined, whereby the fat content can be determined from the detected displacement, (c) said means including a second container to contain a measured volume of source liquid to be drained into the first container when the second container is elevated above the level of the first container, and said means includes a liquid level height gage communicating between said containers and through which liquid may drain to the first container, the height gage supporting the second container spaced above the first container.

3. The combination of claim 2 including a means in the first container to be rotated for dispersing ground meat in the first container.

* * * * *